United States Patent
Andrews et al.

(10) Patent No.: US 10,182,719 B2
(45) Date of Patent: Jan. 22, 2019

(54) METHOD FOR DETERMINING CORNEAL ASTIGMATISM USING OPTICAL COHERENCE TOMOGRAPHY

(71) Applicant: Carl Zeiss Meditec AG, Jena (DE)

(72) Inventors: Delbert Peter Andrews, Oberkochen (DE); Michael Stefan Rill, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 49 days.

(21) Appl. No.: 15/026,206

(22) PCT Filed: Sep. 26, 2014

(86) PCT No.: PCT/EP2014/070642
§ 371 (c)(1),
(2) Date: Mar. 30, 2016

(87) PCT Pub. No.: WO2015/044364
PCT Pub. Date: Apr. 2, 2015

(65) Prior Publication Data
US 2017/0181620 A1    Jun. 29, 2017

(30) Foreign Application Priority Data
Sep. 30, 2013   (DE) .................. 10 2013 219 810

(51) Int. Cl.
*A61B 3/10*    (2006.01)
*A61B 3/103*   (2006.01)
*A61B 3/00*    (2006.01)
*A61B 3/107*   (2006.01)
*A61B 3/117*   (2006.01)

(52) U.S. Cl.
CPC ............ *A61B 3/102* (2013.01); *A61B 3/0025* (2013.01); *A61B 3/1005* (2013.01); *A61B 3/107* (2013.01); *A61B 3/1035* (2013.01); *A61B 3/117* (2013.01)

(58) Field of Classification Search
CPC .. A61B 3/14; A61B 3/12; A61B 3/145; A61B 3/102; A61B 3/1225
(Continued)

(56) References Cited

U.S. PATENT DOCUMENTS

2007/0291228 A1* 12/2007 Huang .................. A61B 3/107
                                                           351/212
2008/0055543 A1*  3/2008 Meyer .................. A61B 3/102
                                                           351/205
(Continued)

FOREIGN PATENT DOCUMENTS

WO    WO 2010/117386 A1    10/2010

OTHER PUBLICATIONS

PCT International Search Report and Written Opinion for International Application No. PCT/EP2014/070642, dated Jan. 27, 2015, 12 pages.
(Continued)

*Primary Examiner* — James Greece
(74) *Attorney, Agent, or Firm* — Patterson Thuente Pedersen, P.A.

(57) ABSTRACT

A method for detecting refractive errors in the eye that are attributable to a suboptimal surface shape of the front surface and/or rear surface of the cornea. An OCT volume scan and/or one or more OCT line scans of the front eye section are carried out; using the measured values, the front and rear surface of the cornea are detected by an edge detection process; the topography of the front and rear surface of the cornea are determined; and refractive errors are determined from said topographies.

9 Claims, 2 Drawing Sheets

(58) Field of Classification Search
USPC .................................. 351/200, 205, 206, 246
See application file for complete search history.

(56) References Cited

U.S. PATENT DOCUMENTS

| | | | |
|---|---|---|---|
| 2009/0168017 A1* | 7/2009 | O'Hara ................. | A61B 3/102 351/205 |
| 2010/0152847 A1 | 6/2010 | Padrick et al. | |
| 2011/0299034 A1* | 12/2011 | Walsh .................... | A61B 3/102 351/206 |
| 2012/0140174 A1 | 6/2012 | Hee et al. | |

OTHER PUBLICATIONS

English translation of PCT International Search Report for International Application No. PCT/EP2014/070642, dated Jan. 27, 2015, 3 pages.

DE Search Report for DE 10 2013 008 532.2, dated Sep. 1, 2014, 8 pages.

Partial English translation of DE Search Report for DE 10 2013 008 532.2, dated Sep. 1, 2014, 5 pages.

Maolong Tang et al: "Corneal power measurement with Fourier-domain optical coherence tomography", Journal Cataract and Refractive Surgery, Surgery, Fairfax, VA, US, vol. 36, No. 12, Jul. 9, 2010 (Jul. 9, 2010), pp. 2115-2122, XP028170034, ISSN: 0886-3350, DOI: 10.1016/J.JCRS.2010.07.018 [retrieved on Sep. 27, 2010].

Young Hoon Hwang et al: "Astigmatism and optical coherence tomography measurements", Graefe's Archive for Clinical and Experimental Ophthalmology, vol. 250, No. 2, Feb. 1, 2012 (Feb. 1, 2012), pp. 247-254, XP055162431, ISSN: 0721-832X, DOI: 10.1007/s00417-011-1788-4.

International Preliminary Report on Patentability for corresponding International Application No. PCT/EP2014/070642 dated Apr. 14, 2016.

\* cited by examiner

METHOD FOR DETERMINING CORNEAL ASTIGMATISM USING OPTICAL COHERENCE TOMOGRAPHY

RELATED APPLICATIONS

This application is a National Phase entry of PCT Application No. PCT/EP2014/070642 filed Sep. 26, 2014, which application claims the benefit of priority to German Application No. 10 2013 219 810.8, filed Sep. 30, 2013, the entire disclosures of which are incorporated herein by reference.

FIELD OF THE INVENTION

The present invention relates to a method for determining refractive errors in the eye, which are due to a sub-optimal surface shape of the anterior surface and/or posterior surface of the cornea of an eye. In particular, the method is used for determining corneal astigmatism using optical coherence tomography.

BACKGROUND

Refractive errors in the eye can be attributed inter alia to refractive errors in the eye lens or to a sub-optimal surface shape of the anterior and posterior sides of the cornea. The refractive error of the eye lens is usually calculated from the subjectively determined total error of the eye and the refractive properties of the cornea.

According to the known prior art, various methods exist to determine the two surface shapes and the thickness of the cornea.

With a slit lamp microscope, one of the most important exploratory devices in ophthalmology, the cornea can generally be subjected only to a qualitative examination by an ophthalmologist or optometrist. The slit of light projected onto the cornea creates an optical section through the cornea, which is viewed with different zoom levels. Through various methods of lighting (diffuse, direct, focal, indirect, regressed, lateral, etc.) and variable light slit widths, it is possible in addition to the anterior portion of the eye to also inspect the middle and posterior portions of the eye. However, determining the surface shapes and the thickness of the cornea is not possible.

For determining the surface shapes and/or thickness of the cornea, current systems use elaborate measurement and evaluation methods. Some systems are only suitable for such tasks.

For example, a pachymeter is used exclusively for measuring corneal thickness in the human eye. Firstly, the determination of the corneal thickness is relevant for the correct determination of the intraocular pressure by tonometry. Secondly, pachymetry plays a further important role in preparation for various eye surgeries.

Here, the following two different methods are generally used:
- non-contact optical measurement (optical coherence pachymeter, OCP) and
- determination by ultrasound, wherein a small ultrasound transducer is placed on the cornea.

In contrast, the ophthalmometer (or keratometer) is an instrument for measuring the surface curvature of the cornea of the eye, as well as determining the corneal curves (keratometry). The instrument allows the measuring of the virtual image and thus a conclusion regarding the curvature of the reflecting surface. Here, a lighted object is placed at a known distance and the reflection of the cornea is observed. This method of measurement is currently used primarily in ophthalmic optics in the fitting of contact lenses, wherein the ophthalmometer is increasingly being replaced by a development thereof, namely the video keratometer.

Another computer-assisted measuring system for the precise measurement of the corneal surface is represented by the keratograph or corneal topographer. Here, the curvature of the cornea, thus the anterior ocular surface, is detected across a large area, which corresponds to a count of approximately 22,000 measurement points. For this purpose, test marks are projected onto the cornea in the form of a ring, and the mirror image thereof is used to calculate the corneal curvature. The curvature distribution can now be calculated from the deviation of these ring images from the ideal spherical shape, and a three-dimensional "map" of the cornea can be determined by conversion of the measurement data.

Modern imaging corneal tomography systems are based, for example, on rotating Scheimpflug cameras or scanning slit systems. Through the combination with Placido discs, the field of imaging, in particular of the anterior segment of the eye, can be significantly improved. These new tomographs create three-dimensional models of the cornea and allow the direct measurement of both corneal surfaces.

The currently available systems have the common disadvantage that they can generally only characterize the anterior portion of the eye and that they are only suitable for such tasks.

The object of the present invention is to further develop or supplement the present ophthalmologic devices such that therewith, in addition to the existing measurement tasks, a determination of the refractive errors in the eye due to a sub-optimal anterior and/or posterior surface shape of the cornea is possible.

This object is achieved by the inventive method for determining refractive errors in the eye that can be traced to a sub-optimal surface shape of the anterior and/or posterior surface of the cornea, in that an OCT volume scan and/or OCT line scan of the anterior segment of the eye is performed, that anterior and posterior surfaces of the cornea are detected from the measured values through edge detection and topographies of refractive errors are determined therefrom.

The proposed method is used for determining refractive errors in the eye, which are due to a sub-optimal surface shape of the anterior and/or posterior side of the cornea. Because the inventive method is based on OCT scans, it thus expands the scope of application of pure standard OCT systems and integrated OCT systems. A prerequisite here is that the OCT systems used are designed for the examination of the anterior ocular segment, which is usually already the case in systems used in ophthalmology. Furthermore, the OCT systems should have different scanning modes, the scan directions of which can be individually customized. Here, the OCT systems may be based both on "time domain" as well as "frequency domain" methods, and in particular also based on a "swept source" system.

BRIEF DESCRIPTION OF THE DRAWINGS

The invention will be described in further detail below with reference to exemplary embodiments.

DETAILED DESCRIPTION

In the inventive method for determining refractive errors in the eye that can be traced to a sub-optimal surface shape of the anterior and/or posterior surface of the cornea, an OCT volume scan and/or one or more OCT line scans of the anterior segment of the eye are performed, the anterior and posterior surfaces of the cornea are detected from the measured values through edge detection, the topographies of the anterior and posterior surfaces of the cornea are detected and refractive errors are determined from these topographies.

According to an example embodiment of the invention, the thickness of the cornea can be determined in addition to the topography of the anterior and posterior surfaces.

Using an OCT scan of the anterior segment of the eye, the surface and thickness of the cornea can be determined at any desired point through image analysis, in particular through edge detection. Analogous to the Scheimpflug or Placido ring systems, surface and curvature gradient maps can be derived therefrom, from which in turn refractive aberrations in the eye can be determined.

Here, both aberrations designated as "normal" (nearsightedness, farsightedness and astigmatism) and so-called higher-order aberrations can be determined. The "normal aberrations" of the eye can be compensated by spherical or cylindrical correction with glasses. In contrast, one could imagine the higher-order aberrations more simply as tiny irregularities which prevent that all incident light rays are focused precisely on the point of sharpest vision. A correction is thus hardly possible.

According to a first example embodiment of the inventive method, in astigmatic eyes an OCT ring scan of the anterior segment of the eye is performed and the extreme values are detected from the measured values of the folded ring scan through edge detection, wherein the minima represent the steep meridian axis and the maxima represent the flat meridian axis of the astigmatism. Here, the determination of the minima and maxima of the OCT ring scan may take place manually or automatically. According to example embodiments, the OCT ring scan takes place concentrically to the apex of the eye.

According to example embodiments of the invention, the characterization of an astigmatic eye is particularly simple. For this purpose, the cross-section of the cornea is measured along a ring which is concentric to the apex of the eye.

Figure 1:
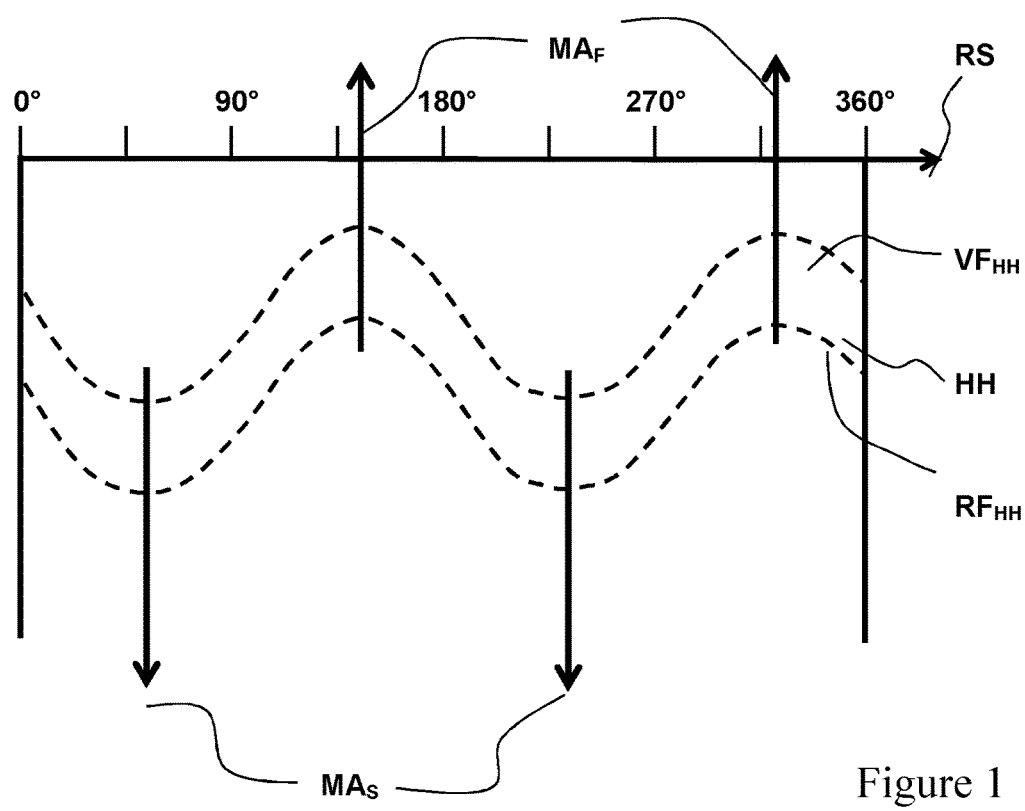
FIG. 1: shows the OCT signal of a folded ring scan of the eye to be examined with the curves of the cornea recognized by edge detection.

To this end, FIG. 1 shows the folded ring scan of an eye to be examined with the curves of the cornea detected by edge detection. The OCT ring scan (360°) is realized along a line RS, which is concentric with the apex AP of the eye A (see also FIG. 2). As can be seen in FIG. 1, the anterior surface $VF_{HH}$ and posterior surface $RF_{HH}$ of the cornea HH of the eye A vary sinusoidally after the "unfolding" of the OCT signal in the case of an (astigmatic) eye A. Here, the minima characterize the steep meridian axis $MA_S$ and the maxima characterize the flat meridian axis $MA_F$ of the astigmatic eye. Thus, the meridian axes of the astigmatic eye can be read directly from the OCT ring scan.

Figure 2:
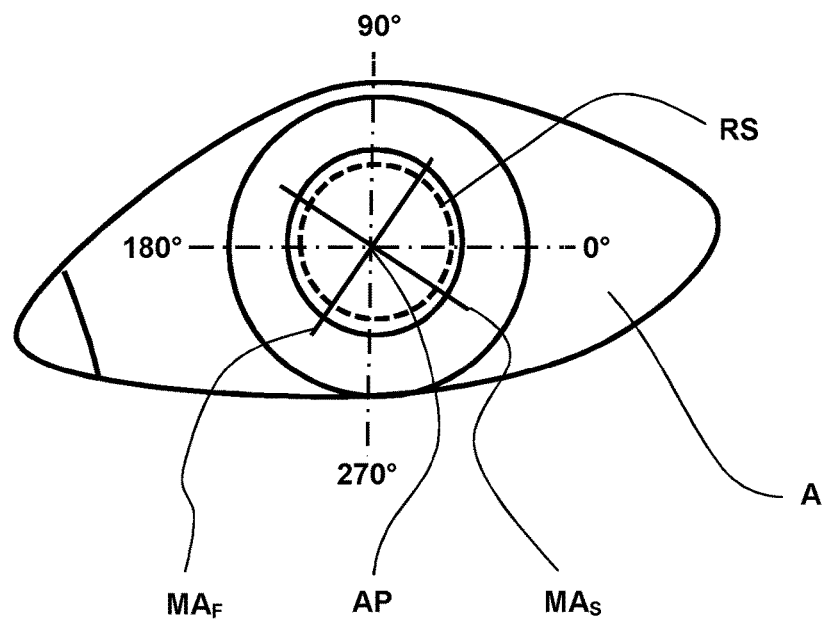
FIG. 2: shows the eye to be examined with plotted ring scan and the meridian axis of the eye determined therefrom

FIG. 2 shows the eye to be examined with plotted OCT ring scan and the meridian axes of the astigmatic eye determined therefrom. In accordance with FIG. 1, FIG. 2 shows both the line RS of the OCT ring scan, lying concentrically to the apex AP of the eye A, as well as the two meridian axes $MA_S$ and $MA_F$ of the astigmatic eye. The degrees can be taken, where the beginning and the end of the of the OCT ring scan lie.

According to a further example embodiment of the inventive method, B-scans are realized along this meridian axis, the anterior and posterior surfaces of the cornea are detected from the measured values by edge detection, the topography of said anterior and posterior surfaces determined and the cylinder refractive powers are determined. For determining the cylinder refractive powers, circles are fitted onto the corneal curvatures in order to detect the maximal and minimal refractive power of the cornea.

Figure 3:
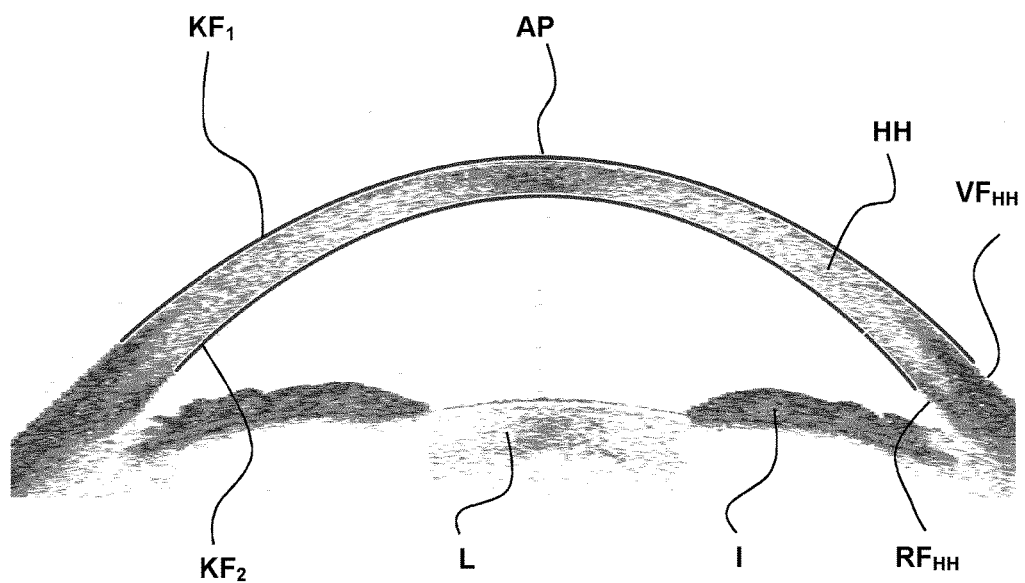
FIG. 3: shows the cornea reconstructed from a B-scan along the meridian axis, with circle fits at the anterior and posterior sides.

To this end, FIG. 3 shows the cornea reconstructed from a B-scan along the meridian axis, with circle fits at the anterior and posterior sides. FIG. 3 shows the following anterior ocular segments, detected from the B-scan: Cornea HH with apex AP, iris I and ocular lens L. For determining the cylinder refractive powers, corresponding circles $KF_1$ and $KF_2$ are fitted on the anterior surface $VF_{HH}$ and the posterior surface $RF_{HH}$ of the cornea HH.

According to a particularly advantageous example embodiment of the inventive method, for intraoperative determination of the axial position of an implanted toric intraocular lens (IOL for short), the extreme values of the curves of the cornea and the implanted toric IOL are detected from the folded OCT ring scan of the anterior segment of the eye by application of edge detection, and the relative phase difference thereof is calculated.

The calculated relative phase difference is used to align the implanted toric IOL with respect to the cornea, wherein an ideal alignment is present when the relative phase difference is 180°.

In the event that the current position of the implanted toric IOL is known, the detection of the meridian axes of the IOL can be omitted. To detect the current alignment of the toric IOL more easily, it is advantageous to mark the meridian axes of the IOL prior to the implantation thereof.

According to example embodiments of-the inventive solution, a method is provided with which the refractive errors in the eye which can be attributed to a sub-optimal surface shape of the anterior and/or posterior surfaces of the cornea can be determined. For this purpose, an OCT volume scan and/or one or more OCT line scans of the anterior segment of the eye are performed, the anterior and posterior surfaces of the cornea are detected from the measured values through edge detection, the topographies of the anterior and posterior surfaces of the cornea are detected and refractive errors are determined from these topographies.

Because the inventive method is based on OCT scans, it thus expands the scope of application of pure standard OCT systems and integrated OCT systems. A prerequisite here is that the OCT systems used are designed for the examination of the anterior ocular segment. The OCT systems used in ophthalmology are generally in the position to model all optical components of the eye in one measuring run; either by stringing together individual scans or through the use of the swept source approach, which can realize a total eye scan.

Furthermore, the OCT systems should have different scanning modes, the scan directions of which can be individually customized. Here, the OCT systems may be based both on "time domain" as well as "frequency domain" methods, and in particular also based on a "swept source" system.

With the disclosed method, ophthalmologic devices are thus further developed or supplemented such that, in addition to the existing measurement tasks, a determination of the refractive errors in the eye due to a sub-optimal anterior and/or posterior surface shape of the cornea is possible.

Example embodiments of the inventive solution provides a fast and simple method for determining refractive errors in the eye by application of OCT. Together with OCT pachymetry measurements (determination of corneal thickness), the method can be used for a correction of astigmatism by the making of incisions in the region of the limbus, for example limbal relaxing incisions by application of fs laser.

A particular advantage of the disclosed method for determining refractive errors in the eye that are due to a sub-optimal surface shape of the anterior surface and/or posterior surface of the cornea of an eye can be seen in that the meridian axes of an astigmatic eye can be read directly from the OCT ring scan.

The invention claimed is:

1. A method of determining refractive errors in the eye related to a sub-optimal surface shape of the anterior and/or posterior surface of the cornea, comprising:
    performing an OCT volume scan, one or more line scans or a combination of the OCT volume scan and the one or more line scans of an anterior segment of an eye;
    detecting the anterior and posterior surfaces of the cornea from measured values through edge detection;
    determining topographies of the anterior and posterior surfaces of the cornea; and determining the refractive errors from the topographies;
    in astigmatic eyes, performing an OCT ring scan of the anterior segment of the eye and detecting extreme values of a curvature of the cornea from the measured values of the folded ring scan through edge detection;
    detecting the extreme values as minima and maxima and determining the minima and the maxima of the OCT ring scan either manually or automatically; and
    for determining the cylinder refractive powers, fitting circles onto the corneal curvatures to detect maximal and minimal refractive power of the cornea; or for determining axes of astigmatism from the determined minima and maxima of the OCT ring scan.

2. The method according to claim 1, further comprising determining a thickness of the cornea in addition to the topographies of the anterior and posterior surfaces.

3. The method according to claim 1, further comprising performing the OCT ring scan concentric to an apex of the cornea.

4. The method according to claim 1, further comprising:
    taking B-scans along meridian axes;
    detecting, the anterior and the posterior surfaces of the cornea from measured values by edge detection;
    determining the topography of said anterior and the posterior surfaces; and
    determining cylinder refractive powers.

5. The method according to claim 1, further comprising:
    taking B-scans along meridian axes;
    detecting, the anterior and the posterior surfaces of the cornea from measured values by edge detection;
    determining the topography of said anterior and the posterior surfaces; and
    determining cylinder refractive powers.

6. The method according to claim 1, further comprising, for intraoperative determination of the axial position of an implanted toric IOL, detecting the extreme values of curves of the cornea and the implanted toric IOL from the folded OCT ring scan of the anterior segment of the eye by edge detection; and
    calculating the relative phase difference thereof.

7. The method according to claim 6, further comprising using the calculated relative phase difference to align the implanted toric IOL with respect to the cornea, wherein an ideal alignment is present when the relative phase difference is 180°.

8. The method according to claim 6, wherein detection of meridian axes of the implanted toric IOL is omitted if a current position thereof is known.

9. The method according to claim 8, further comprising marking the meridian axes of the toric IOL correspondingly before implantation to detect the current position thereof.

* * * * *